(12) United States Patent
Hickingbotham

(10) Patent No.: US 6,730,076 B2
(45) Date of Patent: May 4, 2004

(54) FIBEROPTIC PROBE TIP

(75) Inventor: Dyson W. Hickingbotham, Stouchsburg, PA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/962,642

(22) Filed: Sep. 25, 2001

(65) Prior Publication Data

US 2003/0060812 A1 Mar. 27, 2003

(51) Int. Cl.[7] ............................................. A61B 18/18
(52) U.S. Cl. ....................... 606/16; 606/13; 606/205; 606/206; 606/207
(58) Field of Search .................... 606/7, 10, 13–16, 606/27, 32, 41, 51, 52, 159, 205–211; 414/1–7

(56) References Cited

U.S. PATENT DOCUMENTS

| | | | | |
|---|---|---|---|---|
| 4,266,547 A | * | 5/1981 | Komiya ................. 128/303.1 |
| 4,566,438 A | | 1/1986 | Liese et al. |
| 5,169,397 A | * | 12/1992 | Sakashita et al. ............. 606/27 |
| 5,196,005 A | * | 3/1993 | Doiron et al. .................. 606/7 |
| 5,335,648 A | | 8/1994 | Kozawa et al. |
| 5,351,168 A | | 9/1994 | Easley |
| 5,352,221 A | | 10/1994 | Fumich |
| 5,360,425 A | | 11/1994 | Cho |
| 5,431,646 A | | 7/1995 | Vassiliadis et al. |
| 5,534,000 A | * | 7/1996 | Bruce ......................... 606/15 |
| 5,549,627 A | * | 8/1996 | Kieturakis ................... 606/206 |
| 5,653,716 A | * | 8/1997 | Malo et al. .................. 606/139 |
| 5,667,472 A | | 9/1997 | Finn et al. |
| 5,681,264 A | | 10/1997 | Ryan, Jr. |
| 5,746,769 A | * | 5/1998 | Ton ............................ 606/206 |
| 5,916,149 A | | 6/1999 | Ryan, Jr. |
| 6,135,993 A | | 10/2000 | Hussman |
| 6,187,026 B1 | * | 2/2001 | Devlin et al. ................ 606/205 |
| 6,254,530 B1 | | 7/2001 | Ryan, Jr. |
| 6,488,695 B1 | * | 12/2002 | Hickingbotham ........... 606/206 |

FOREIGN PATENT DOCUMENTS

JP    405212050 A  *  8/1993  ............ A61N/5/06

* cited by examiner

Primary Examiner—Michael Peffley
Assistant Examiner—Ahmed M Farah
(74) Attorney, Agent, or Firm—Jeffey S. Schira

(57) ABSTRACT

A probe tip having a surgical tool manufactured from a light transmissive material. Such a construction eliminates the need for a separate fiberoptic and surgical tool. If desired, the probe tip may be used in combination with a surgical probe having an actuation handle made from springy material having a memory. Squeezing the handle causing the actuation device to elongate, thereby causing movement in the probe tip. The probe handle of the present invention may be held and actuated in any position.

7 Claims, 2 Drawing Sheets

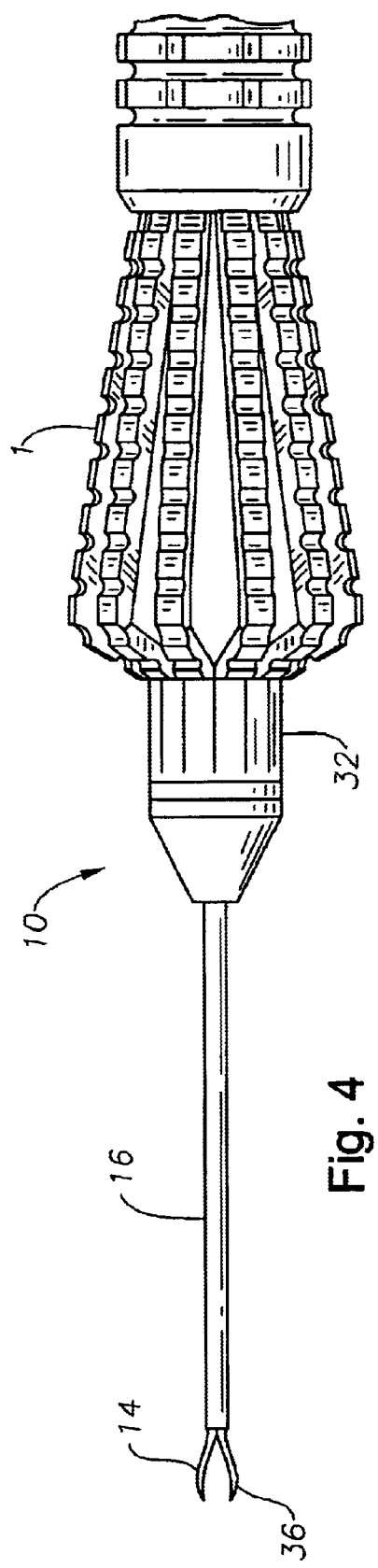
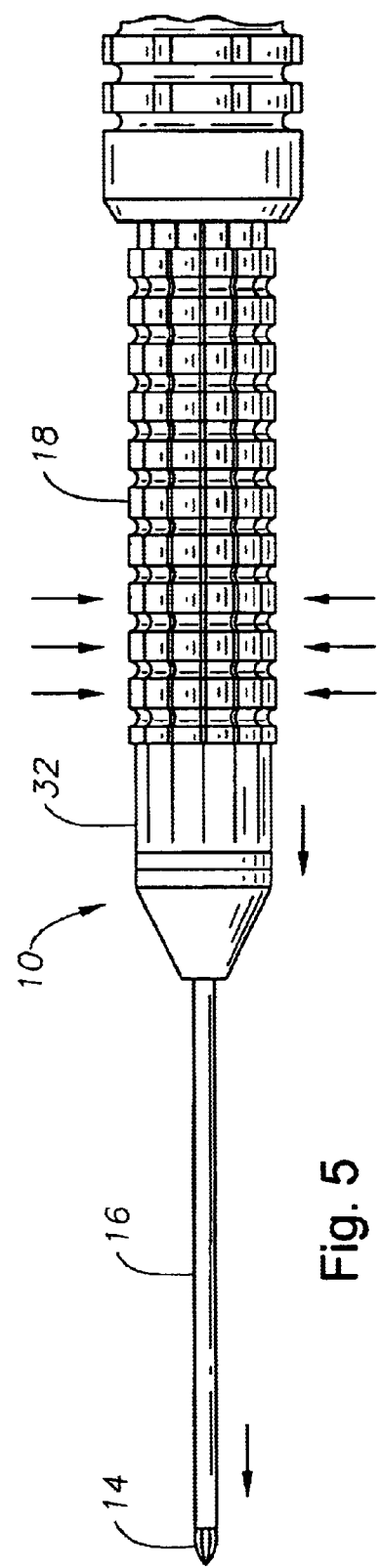

FIBEROPTIC PROBE TIP

BACKGROUND OF THE INVENTION

This invention relates generally to the field of surgical probes and, more particularly, to ophthalmic surgical probes.

During ophthalmic microsurgery, and in particular, surgery of the retina and vitreous, it is often necessary to dissect, cut, delaminate or otherwise manipulate delicate tissues within the eye. Microsurgical tools, such as microscissors, micro forceps and other devices generally are used for such manipulations. In order to visualize the surgical field, additional illumination is needed. Various fiberoptic probes have been developed to provide illumination to the back of the eye. See, for example, U.S. Pat. No. 5,351,168 (Easley), the entire contents of which being incorporated herein by reference.

The difficulty in introducing multiple probes and/or surgical tools into a surgical site as small as the eye has led to combining the fiberoptic illuminator and the surgical tool onto the same probe tip. See, for example, U.S. Pat. Nos. 5,681,264, 5,916,149 and 6,254,530, the entire contents of which being incorporated herein by reference. While these devices work well, the probe tip must still be large enough to contain both a fiberoptic and a surgical pic, forceps or the like. In addition, these combination devices can cause shadows that make it difficult to see.

Accordingly, a need continues to exist for a probe tip that combines the surgical tool and fiberoptic illuminator.

BRIEF SUMMARY OF THE INVENTION

The present invention improves upon the prior art by providing a probe tip having a surgical tool manufactured from a light transmissive material. Such a construction eliminates the need for a separate fiberoptic and surgical tool. If desired, the probe tip may be used in combination with a surgical probe having an actuation handle made from springy material having a memory. Squeezing the handle causing the actuation device to elongate, thereby causing movement in the probe tip. The probe handle of the present invention may be held and actuated in any position.

Accordingly, one objective of the present invention is to provide a probe tip that combines a surgical tool with a fiberoptic illuminator.

Another objective of the present invention is to provide a probe tip that combines a surgical tool with a fiberoptic illuminator without causing shadows in the surgical field.

Another objective of the present invention is to provide an inexpensive probe tip.

Still another objective of the present invention is to provide a probe having a relatively small and compact probe tip.

These and other advantages and objectives of the present invention will become apparent from the detailed description and claims that follow.

BRIEF DESCRIPTION OF THE DRAWING

FIG. 4 is a top plan view of one embodiment of a probe that may be used with the probe tip of the present invention shown in its relaxed stated.

FIG. 5 is a top plan view of one embodiment of a probe that may be used with the probe tip of the present invention shown in its compressed stated.

DETAILED DESCRIPTION OF THE INVENTION

Figure 1:
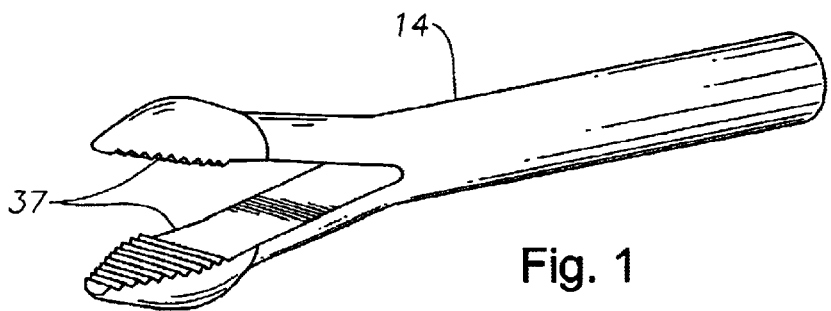
FIG. 1 is an enlarged perspective view of a first embodiment of the probe tip of the present invention.
Figure 2:
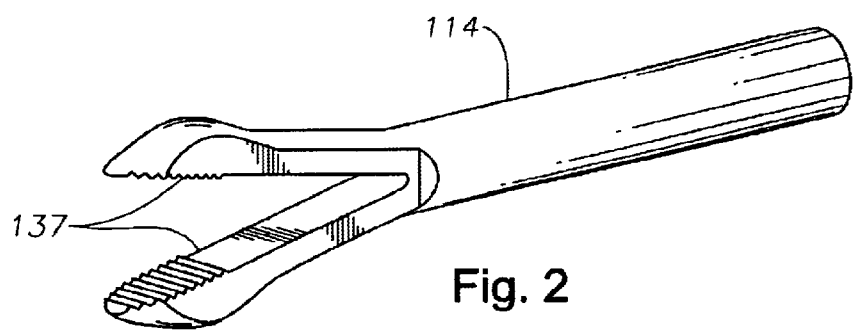
FIG. 2 is an enlarged perspective view of a second embodiment of the probe tip of the present invention.
Figure 3:
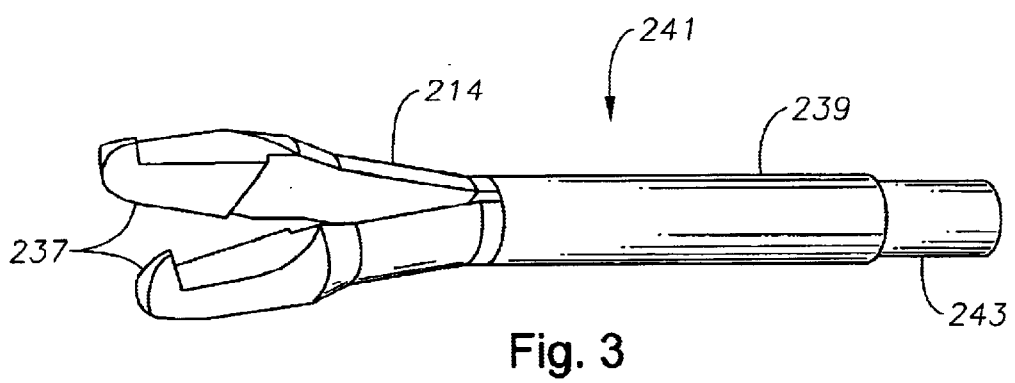
FIG. 3 is an enlarged perspective view of a third embodiment of the probe tip of the present invention.

As seen in FIGS. 1–3, tip 14, 114 and 214 may be formed into a variety of surgical tools, such as forceps, pics and other desired devices. Tip 14, 114 and 214 preferably is made from splitting a nylon monofilament or other suitable light transmissive material. The split monofilament can be formed into a variety of tools or shapes such as jaws 37 and 137 or jaws/pic 237 using heat and an appropriate forming jig, such devices being well-known in the art. As best seen in FIG. 3, tip 214 can then be bonded to fiberoptic 243 by cyanoacrylate adhesive and polyamide sleeve 239 so as to provide an optical interface between tip 214 and the fiberoptic. Suitable fiberoptic(s) 243 are well-known in the art. The combination fiberoptic/tip 241 may then be assembled into a suitable actuation probe in the manner described below. Tips 14, 114 and 214 illustrated in FIGS. 1–3 are representative devices that may used with the present invention. One skilled in the art will recognize that other surgical tools and devices may be made following the teachings contained herein.

In use, tip 14, 114 or 214 may be assembled as part of any suitable actuation probe, for example, the probe disclosed in U.S. patent application Ser. No. 09/641,066, filed Aug. 17, 2000, the entire contents of which being incorporated herein by reference. When tip 14, 114 or 214 is part of such a probe assembly 10, the operation of assembly 10 is best seen in FIGS. 4 and 5. When actuation handle 18 is in its relaxed stated, distal end 36 of tip 14, for example, protrudes a relatively large amount from tube 16. By preventing rearward movement of actuation handle 18, squeezing of actuation handle 18 (as seen in FIG. 5) forces front portion 32 of actuation handle 18 forward. The forward movement of front portion 32 of actuation handle 18 is transferred to tube 16, causing tube 16 to slide forward over distal end 36 of probe tip 14, probe tip 14 being telescopically received in tube 16, thereby compressing together distal tip 36. The amount of movement of tube 16 over distal tip 36 can be controlled easily by varying the outer diameter of actuation handle 18 in its relaxed stated, with larger diameters causing greater longitudinal movement.

Figure 6:
FIG. 6 is an enlarged perspective view of a fourth embodiment of the probe tip of the present invention.

As seen in FIG. 6, tip 314 does not need to be formed with operative jaws, and tip 314 may be formed into any suitable operative tool, such as a pic, in the manner discussed above.

This description is given for purposes of illustration and explanation. It will be apparent to those skilled in the relevant art that changes and modifications may be made to the invention described above without departing from its scope or spirit.

I claim:

1. A surgical device, comprising:
   a) a tip made from a light transmissive material;
   b) a forceps formed on the tip from the light transmissive material; and
   c) a fiberoptic mechanically connected to the tip.

2. The probe of claim 1 wherein light transmissive material is a nylon monofilament.

3. The probe of claim 1 wherein the fiberoptic is connected to the tip by an adhesive and a sleeve.

4. A probe, comprising:
a) an actuation handle having a first diameter and a first length in its relaxed stated and a second diameter and a second length in its compressed state, the first diameter being larger than the second diameter and the second length being longer than the first length;
b) a tube fixed to a distal end of the actuation handle; and
c) a probe tip made from a light transmissive material, the probe tip being mechanically connected to a fiberoptic and having a forceps telescopically received through the tube and fixed to an end sleeve located on a proximal end of the actuation handle so that compression of the actuation handle causes compression of the forceps.

5. The probe of claim 4 wherein the light transmissive material is a nylon monofilament.

6. A surgical device, comprising:
a) a tip made from a light transmissive material;
b) a pic formed on the tip from the light transmissive material; and
c) a fiberoptic mechanically connected to the tip.

7. A surgical device, comprising:
a) a tip made from a light transmissive material;
b) jaws formed on the tip from the light transmissive material; and
c) a fiberoptic mechanically connected to the tip.

* * * * *